United States Patent [19]

Matsumoto

[11] Patent Number: 6,007,776
[45] Date of Patent: Dec. 28, 1999

[54] LIQUID MEASUREMENT INSTRUMENT

[75] Inventor: Toru Matsumoto, Tokyo, Japan

[73] Assignee: NEC Corporation, Tokyo, Japan

[21] Appl. No.: 09/093,192

[22] Filed: Jun. 8, 1998

[30] Foreign Application Priority Data

Jun. 9, 1997 [JP] Japan .................................. 9-151238

[51] Int. Cl.$^6$ .................................................. G01N 35/10
[52] U.S. Cl. .......................... 422/68.1; 422/81; 422/82; 422/100; 422/103; 436/8; 436/179; 436/180; 604/249
[58] Field of Search .............................. 422/68.1, 81, 82, 422/100, 103; 436/8, 53, 174, 180, 179; 73/53.01, 431, 866.1, 866.5; 604/249

[56] References Cited

U.S. PATENT DOCUMENTS

| | | | |
|---|---|---|---|
| 3,990,853 | 11/1976 | Godin | 422/82 |
| 4,208,372 | 6/1980 | Huber | 422/81 |
| 5,254,313 | 10/1993 | Kuroda et al. | 422/81 |
| 5,486,478 | 1/1996 | Kuriyama | 422/82 |
| 5,879,629 | 3/1999 | Capuano et al. | 422/82 |

FOREIGN PATENT DOCUMENTS

| | | |
|---|---|---|
| 62-24139 | 2/1987 | Japan . |
| 62-240848 | 10/1987 | Japan . |
| 62-250355 | 10/1987 | Japan . |
| 1-101968 | 4/1989 | Japan . |
| 1-201163 | 8/1989 | Japan . |
| 3-273153 | 12/1991 | Japan . |
| 4-341241 | 11/1992 | Japan . |
| 7-56001 | 12/1995 | Japan . |

*Primary Examiner*—Gary K. Graham
*Attorney, Agent, or Firm*—Young & Thompson

[57] ABSTRACT

A measurement instrument for analyzing a body fluid of a human body comprises a casing having a pair of liquid inlets and a pair of liquid outlets, and a sensor assembly slidably telescoped in the casing. The sensor assembly comprises a pair of liquid passages each aligned with a corresponding one the pair of liquid inlets and a corresponding one of the pair of liquid outlets at a specified position of the sensor assembly. One of the liquid passages is associated with a sensor for being a specific ingredient in the body fluid.

13 Claims, 9 Drawing Sheets

LIQUID MEASUREMENT INSTRUMENT

BACKGROUND OF THE INVENTION (a) Field of the Invention

The present invention relates to a liquid measurement instrument for continuously analyzing particular ingredients in a liquid by using electrochemical analysis and, more particularly, to a liquid measurement instrument suitable for analyzing body fluid such as human blood or other fluids.

(b) Description of the Related Art

A liquid measurement (test) instrument is generally used for analyzing ingredients in body fluid such as human blood. Patent Publication JP-A-1(1989)-101968 describes a conventional test instrument wherein a chemical sensor is used for testing blood ingredients extracted or sampled from a living body.

FIG. 1 shows the conventional test instrument as mentioned above, wherein a catheter 51 for sampling human blood is connected to the test instrument through a connector 54 attached to a first end of the test instrument by a tube 52. The test instrument comprises a chemical sensor 55, a first 3-way cock 56, a second 3-way cock 57, a pressure sensor 58, a flow control valve 59 connected by pipe 53 and arranged in this order from the connector 54 toward the second end of the test instrument to which a reservoir 61 for receiving therein a reference liquid 60 is connected. A pH sensor, a partial-pressure sensor for detecting $PO_2$ or $PCO_2$, an electrolyte sensor for detecting Na, K, Cl or Mg, a protein sensor, a blood sugar sensor or other sensor is used as the chemical sensor 55 depending on the use of the test instrument.

The first 3-way cock 56 is disposed between the chemical sensor 55 and the second 3-way cock 57, with a branch port of the first 3-way cock 56 being connected to a syringe 62. The first 3-way cock either connects the catheter 51 with the second 3-way cock 57, with the syringe 62 being disconnected, or connects the catheter 51 to the syringe 62. The second 3-way cock 57 is disposed between the first 3-way cock 56 and the pressure sensor 58, with a branch port thereof being open to the drain. The second 3-way cock either passes the reference liquid 60 to the chemical sensor 55 or drains the reference liquid 60 from the chemical sensor 55. The flow control valve 59 codes a glass pole 59a having a small axial hole and an elastic tube 59c press-fit onto the glass pole 59a and slidably mounted on the pipe 53. When the elastic tube 59c is thrust in a direction normal to the axial direction, a space is provided between the inner wall of the elastic tube 59c and the external wall of the pipe 53, thereby bypassing the reference liquid 60 during a flashing operation.

For flashing the pipe 53, after the catheter 51 is removed from a living body, the reservoir 61 is filled with the reference liquid 60, followed by thrusting the elastic tube 59c to form a bypass for introducing a comparatively large quantity of the reference liquid 60 into the pipe 53. After the reference liquid 60 is drained from the catheter 51 together with air bubbles to clean both the catheter 51 and the pipe 53, the catheter 51 is inserted in the blood vessel of the living body while both the catheter 51 and the pipe 53 are filled with the reference liquid. During this operation, both the 3-way cocks 56 and 57 are set for passing the reference liquid 60 to the catheter 51 through the pipe 53 as shown in FIG. 1.

Then, the second 3-way cock 57 is switched for closing the pipe 53, as shown in FIG. 2, to calibrate the sensor by using the reference liquid 60 and the chemical sensor 55. The calibration data is read through signal lines 64 extending from the chemical sensor 55 by a microcomputer not shown.

Subsequently, the first 3-way cock 56 is switched so that the piston 62a in the syringe 62 is pulled out to introduce the reference liquid 60 into the syringe 62 and introduce blood 63 into the pipe 53 through the catheter 51 by using a negative pressure, as shown in FIG. 3. The chemical sensor 55 disposed for a particular ingredient detects the ingredient in blood 63 and supplies data to the microcomputer.

After the measurement is completed, the blood 63 is returned to the living body by thrusting the piston 62a of the syringe 62. Patent Publication JP-A-62(1987)-24139 describes an automated calibration of a test instrument with a simple configuration.

Referring to FIG. 4, the test instrument described in JP-A-62(1987)-24139 comprises a first reservoir 91 for receiving a carrier liquid 81, a second reservoir 101 for receiving a first reference liquid 82 comprising the carrier liquid and a calibrating substance and a third reservoir 111 for receiving a second reference liquid 83 comprising the carrier liquid and a disturbing substance. Tubes extending from the reservoirs 91, 101 and 111 are connected to an 4-way cock 84 for controlling the direction of liquid flow. The 4-way cock 84 is driven by a servomotor and controlled by an encoder for selecting a desired liquid flow. One port of the 4-way cock 84 is connected to a cell (reactor) 85 having a sensor 87 with a tube 121, and a pump 86 is provided for supplying the liquids from the reservoirs to the cell 85.

FIG. 5 shows a partially cutout perspective view of the cell 85, wherein a sample liquid is supplied through an inlet port 132 and discharged hugh an outlet port 133. Since the outlet port 133 is disposed at a higher position than the inlet port 132, a specified amount of sample liquid stays within the cell 85, with the excess liquid or measured liquid overflowing through the outlet port 133 to a waste tank 88. The sensor 87 comprises thee electrodes including an enzyme electrode 87a attached with a living catalyst such as enzyme, a disturbance electrode 87c for detecting a disturbance substance and a counter electrode 87b. The three electrodes 87a, 87b and 87c are connected to respective external electrodes by connectors 87d. On the top of the cell 85, an elastic cap 131 is inserted in the central area, and a liquid inlet 131a is provided in the center of the elastic cap 131a for supplying sample liquid. The 4-way valve 84 may be such that shown in FIG. 6 instead, wherein the 4-way valve 84 in FIG. 4 is implemented by three individual electromagnetic valves 84a.

Utility Model Publication JM-A-7(1995)-56001 describes a sampling instrument such as shown in FIG. 7. The sampling instrument is dedicated for sampling and comprises a cell (housing) including a funnel area 153, having a sampling port 159 communicated to a suction port 151 with a valve 157, for collecting a body fluid 161 from a living body. In operation, body fluid is first collected by vacuum and introduced to a storage space 160 of the valve 157, then a handle 156 of the valve is operated to align the storage space 160 with an outlet port 165 for takeout of the body fluid. The takeout can be conducted without stopping the vacuum pump or removing a cover.

FIG. 8 shows a modification of the sampling instrument of FIG. 7. The sampling instrument of FIG. 8 is similar to the sampling instrument of FIG. 7 except for a pair of storage spaces 160 provided in a valve 157 and a pair of outlet ports 165 in the modification. In operation, body fluid is introduced to one of the storage spaces 160 from the sampling port 159, then the handle 156 is operated to align the one of the storage spaces 160 to one of the outlet ports 165 and to align the other of the storage spaces 160 with the sampling port 159. This enables to obtain a sampling operation and a takeout operation simultaneously for improvement of the throughput.

The conventional measurement instruments as described above have the following problems.

First, sampling is interrupted in the measurement instruments during cleaning the cell by a buffer solution after measurement and subsequent supplying a new buffer solution into the cell. The sampling is also interrupted by removing a sample liquid from the cell after measurement.

Second, a large quantity of sample liquid must be sampled for measurement because a sensor is installed in a chamber, which results in a large quantity of dead volume.

Third, an inaccurate measurement is caused by the precedent sampling liquid remaining within the cell after the cleaning thereof.

Fourth, the sensor calibration is limited by the facts that the reference liquid cannot be supplied into the cell when both ports are closed for the sampling period and that the sensor must be cleaned by a buffer solution after removing the sample liquid. Especially, cleaning is difficult because of the column configuration of the cell.

SUMMARY OF THE INVENTION

It is therefore an object of the present invention to provide a measurement instrument for analyzing an ingredient in a sample liquid, which is capable of iteratively measuring the ingredients in a small quantity of sample liquid and capable of enabling simple calibration of the sensor.

The present invention provides a measurement instrument comprising a casing having a first liquid inlet and a first liquid outlet opposed to each other and a second liquid inlet and a second liquid outlet opposed to each other, a sensor assembly having a telescope member slidably telescoped in the casing between a first position and a second position, a liquid passage formed in the telescoped member, the liquid passage being aligned with the first liquid inlet and the first liquid outlet at the first position of the telescope member and aligned with the second liquid inlet and the second liquid outlet at the second position of the telescope member, at least one sensor supported by the telescope member and exposed in the liquid passage.

In accordance with the measurement instrument of the present invention, structure of the instrument and switching operation thereof between calibration and measurement are simplified.

The above and other objects, features and advantages of the present invention will be more apparent from the following description, referring to the accompanying drawings.

DESCRIPTION OF THE PREFERRED EMBODIMENTS

Figure 1:
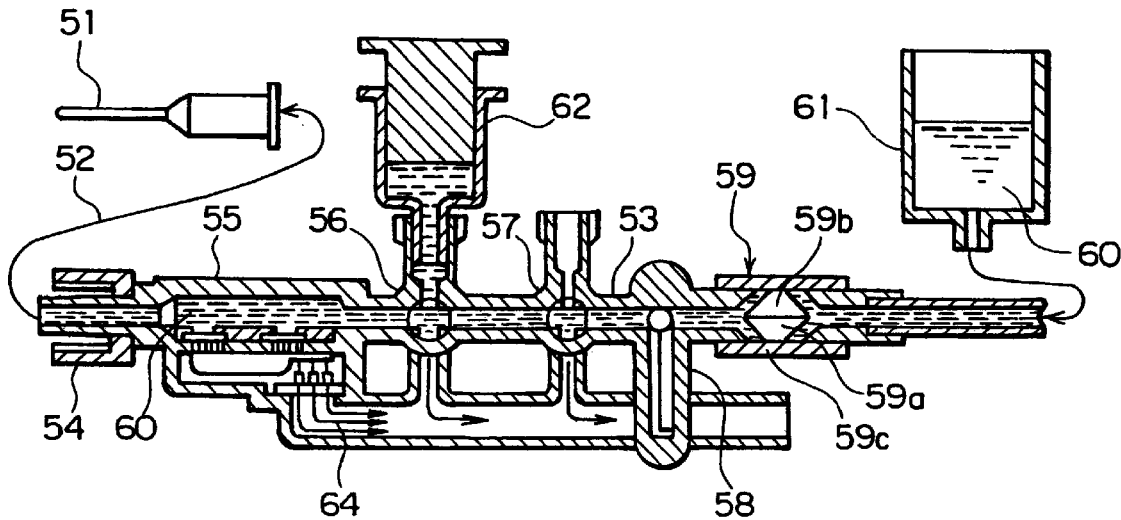
FIG. 1 is a sectional view of a first conventional measurement instrument.
Figure 2:
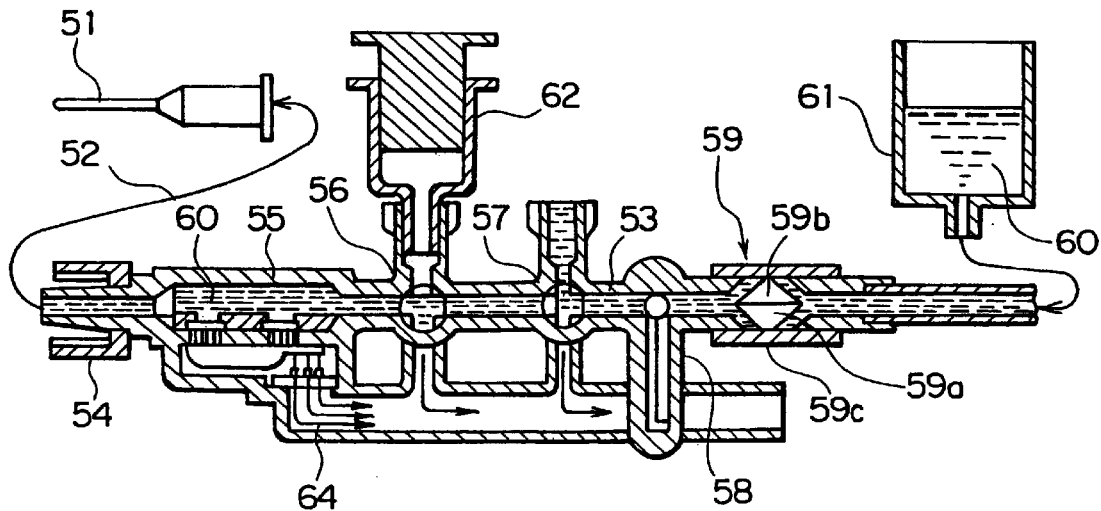
FIG. 2 is another sectional view of the measurement instrument of FIG. 1 during calibration thereof.
Figure 3:
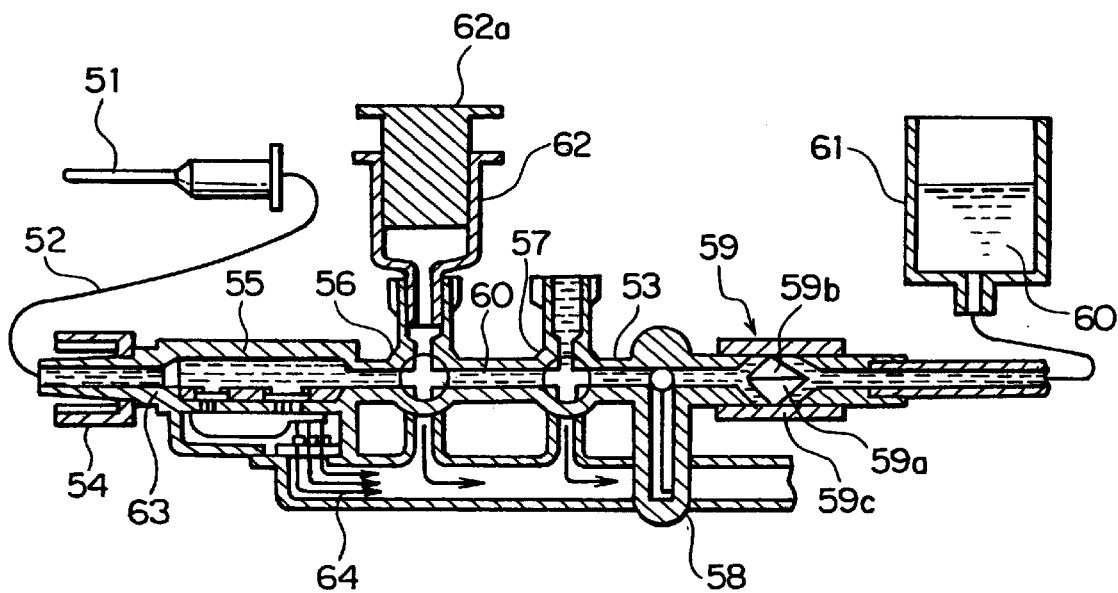
FIG. 3 is another sectional view of the measurement instrument of FIG. 1 during measurement.
Figure 4:
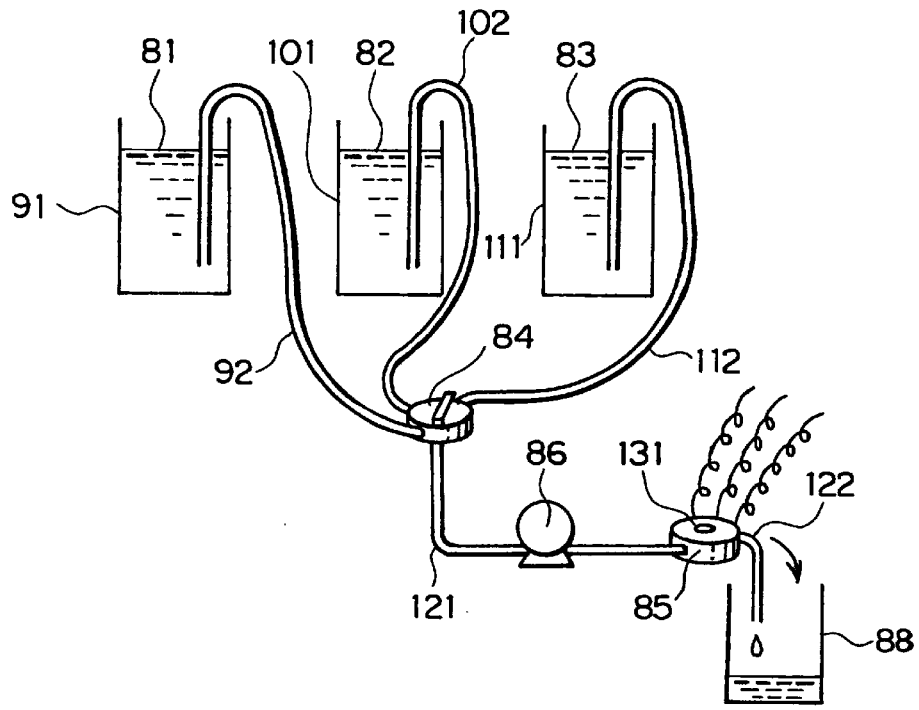
FIG. 4 is a schematic perspective view of a second conventional measurement instrument.
Figure 5:
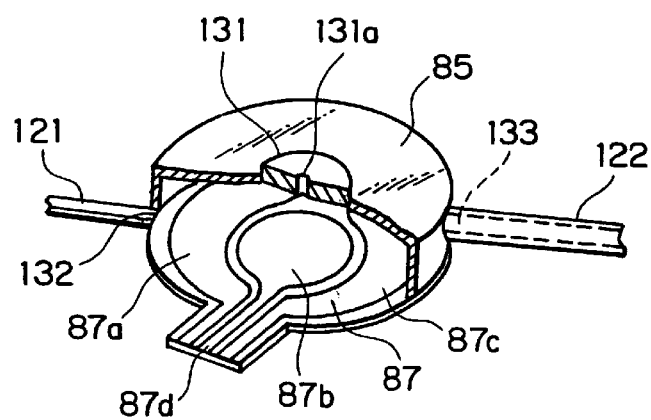
FIG. 5 is a partially cutaway view of the cell shown in FIG. 4.
Figure 6:
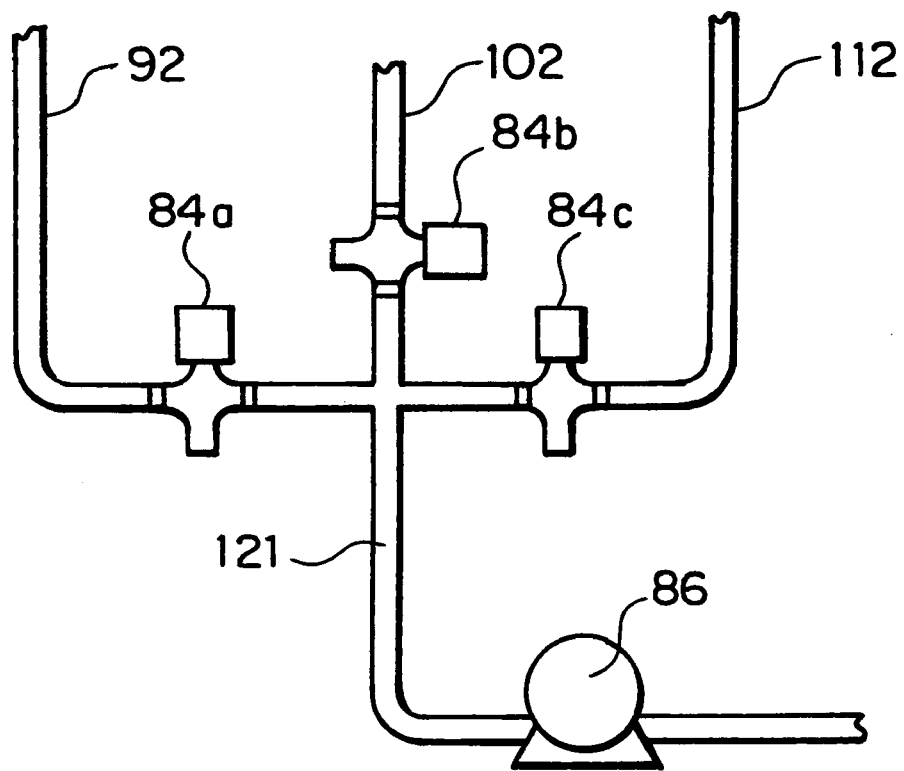
FIG. 6 is a schematic view of a modification of the 4-way cock shown in FIG. 5.
Figure 7:
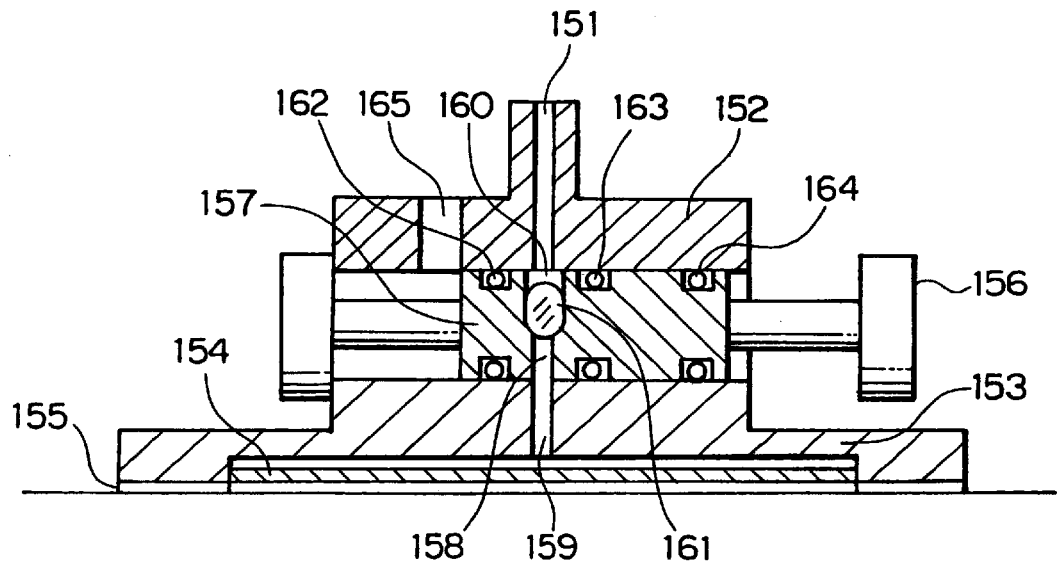
FIG. 7 is a sectional view of a conventional sampling instrument.
Figure 8:
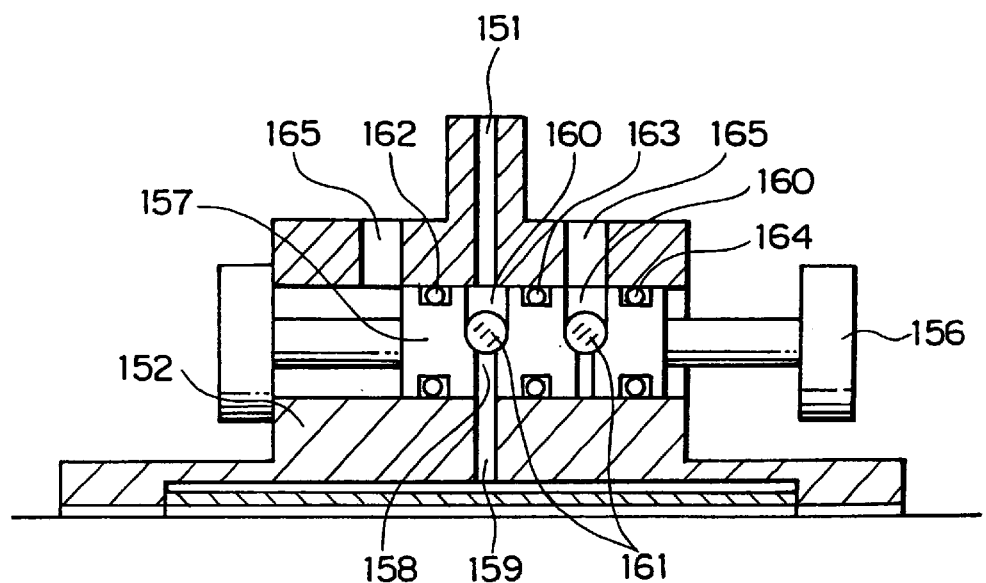
FIG. 8 is a sectional view of a modification of the sampling instrument of FIG. 7.

Now, the present invention is more specifically described with reference to the accompanying drawings, wherein similar constituent elements are designated by the same or similar reference numerals.

Figure 9:
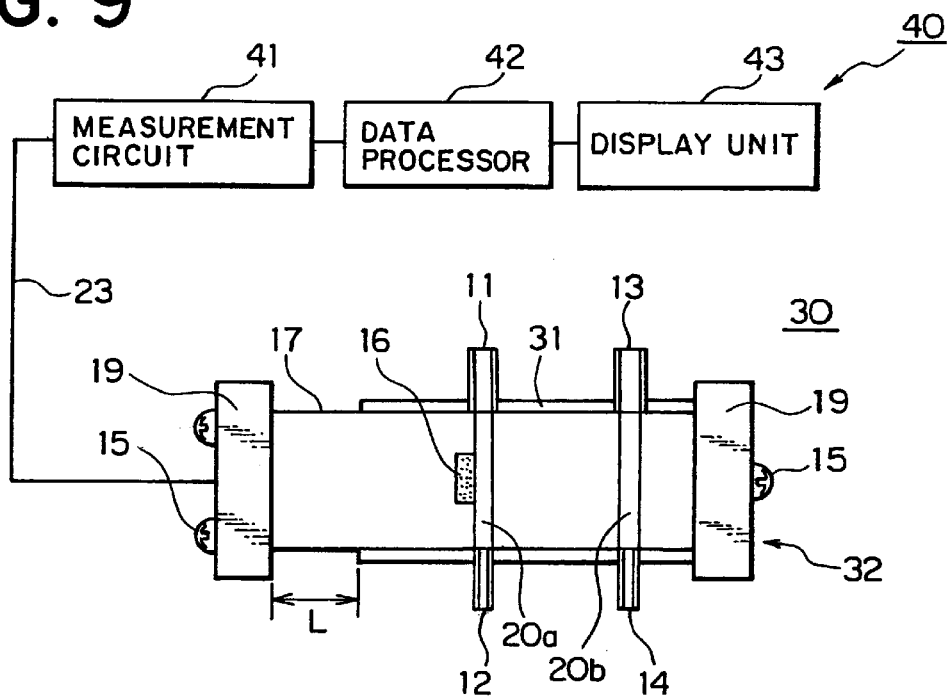
FIG. 9 is a schematic sectional view of a measurement instrument according to a first embodiment of the present invention.

Referring to FIG. 9, a measurement instrument according to a first embodiment of the present invention comprises a measurement cell 30 including a casing 31 having a shape of a hollow hexahedron and a sensor assembly 32 having a shape of substantially solid hexahedron and slidably telescoped in the casing 31, and a circuit block 40 including a measuring circuit 41, a data processor 42 and a display unit 43 and connected to the sensor assembly 32 via wires 23.

The casing 31 has a reference liquid inlet 11 and a reference liquid outlet 12 opposed to each other, and a sample liquid inlet 14 and a sample liquid outlet 13 opposed to each other. The sensor assembly 32 comprises a solid body (telescope member) 17 having therein a first passage 20a and a second passage 20b, which can be communicated with the liquid inlets 11 and 14 and liquid outlets 12 and 13 of the casing 31, a pair of stoppers 19 attached to both ends of the solid body 17 by way of screws 15, and a sensor 16 received in the solid body 17 and exposed in the first passage 20a. The solid body 17 comprises a pair of block pieces coupled together via the screws 15 which attach the stoppers 19 to the solid body 17, as will be described later. The sensor 16 can be taken out or introduced in the solid body 17 by disassembling the solid body 17 using the screws 15. The sensor assembly 32 can be shifted in both directions of the axis of the solid body 17 with respect to the casing 31 and is shown at the left most position (first position) of the sensor assembly 32.

The first and second passages 20a and 20b are communicated with the reference liquid inlet 11 and outlet 12 and sample liquid inlet 14 and outlet 13, respectively, at the first position of the sensor assembly 32, thereby forming liquid paths therethrough. The sensor 16 can measure a specific ingredient in the reference liquid at the first position of the sensor assembly 32, and the ingredient in the sample liquid at a second position at which the sensor assembly 32 is shifted in the right. In this embodiment, the passages 20a and 20b are shown as extending in the direction perpendicular to the sliding direction of the sensor assembly 32. However, the direction of the passages 20a and 20b need not be perpendicular to the sliding direction of the sensor assembly 32.

The sensor 16 is detachably mounted in the solid body 21, with the surface of the sensor 16 being flush with the inner surface of the first passage 20a. The sensor surface may be disposed slightly depressed from the inner surface of the passage 20a. In this configuration, the liquid flows more smoothly in the passage.

Materials for the ports of reference liquid inlet 11, reference liquid outlet 12, sample liquid inlet 14 and sample liquid outlet 13, sensor assembly 32 and casing 31 are not limited to any of the materials, and may be preferably plastic or ceramic-based materials in view of electric insulation, water and chemical resistance, and/or productivity of the instrument.

Preferably, the material for the liquid inlet or outlet of liquid passage may be an antibacterial substance or may be treated with such a substance. The materials for reference liquid inlet 11, reference liquid outlet 12, sample liquid inlet 14, sample liquid outlet 13, and passages 20a and 20b may have hydrophobic property for prevention of attachment of impurities or air bubbles in the liquid.

The sensor 16 may be a chemical sensor of an amperometric or potentiometric detection type, such as for detecting an electrode active material or ions generated by catalytic reaction of an enzyme. Examples of enzyme sensors of amperometric type include sensors for detecting lactic acid, glucose, galactose, sucrose, ethanol, methanol, starch, uric acid, pyruvic acid, cholesterol, choline etc. Examples of sensors of potentiometric type include ion sensitive EFTs for detecting hydrogen-ion (pH), Na-ion, K-ion or Cl-ion concentration.

The first and second passages 20a and 20b may have any sectional configuration and any length provided that a smooth supply, holding and flow of a liquid are assured. Preferably, the passages 20a and 20b may have a round section and straight length as shown in FIG. 9 for reducing void volume. For example, the length may be selected between 10 mm and 50 mm and more preferably at about 30 mm and the diameter may be selected between 0.6 mm and 10 mm, and more preferably at about 2.0 mm.

A spacing between the passages 20a and 20b may be selected in consideration of operability of the instrument and workability of the material.

Figure 10:
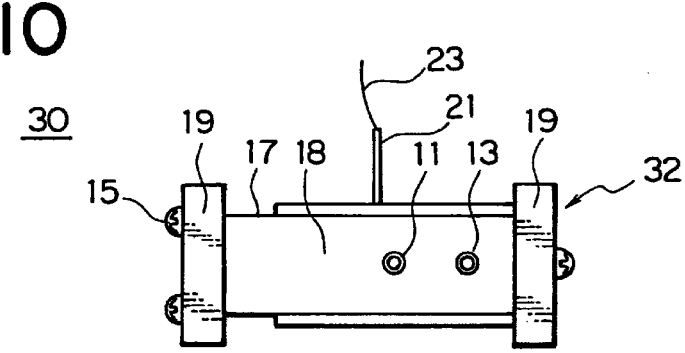
FIG. 10 is a top plan view of the measurement cell shown in FIG. 9.

Referring to FIG. 10 showing the top plan view of the measurement cell 30, a sensor support 21 for supporting the sensor 16 is shown as extending from the sensor assembly 32 through the wall of the casing 31. The sensor support 21 also supports the wire 23 for the sensor 16.

Figure 11:
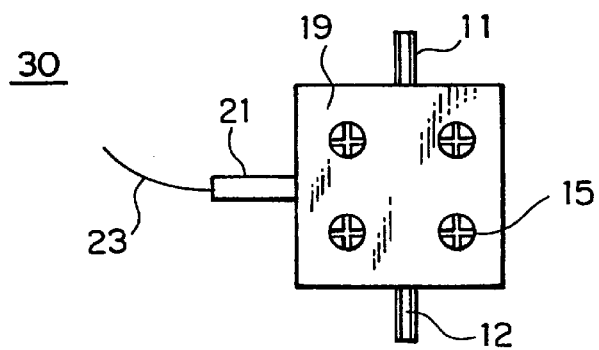
FIG. 11 is an end view of the measurement cell shown in FIG. 9.

Referring to FIG. 11 showing the end view of the measurement cell 30, the stopper 19 is substantially of a square, but not limited to the shape illustrated.

Figure 12:
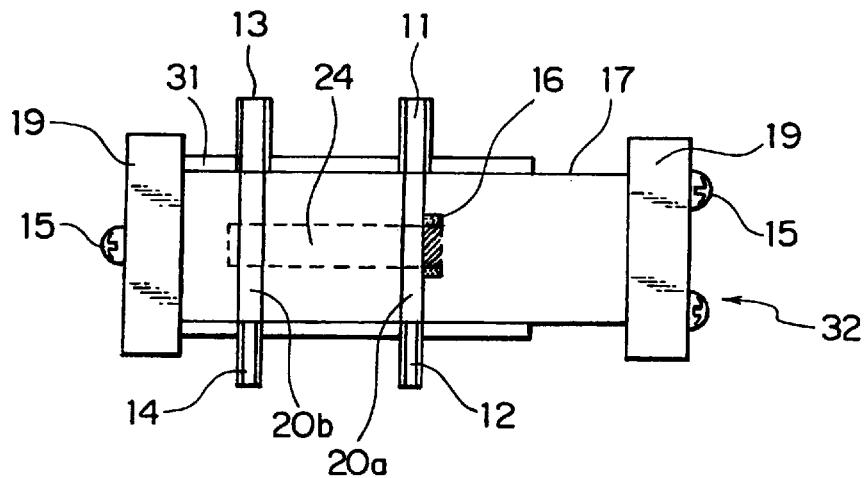
FIG. 12 is a sectional view of the measurement cell shown in FIG. 9 as viewed from the back of the sheet in FIG. 9.

Referring to FIG. 12, the casing 31 has a rectangulr opening 24 for guiding the sensor support 21 during sliding movement of the sensor assembly 32.

Figure 13:
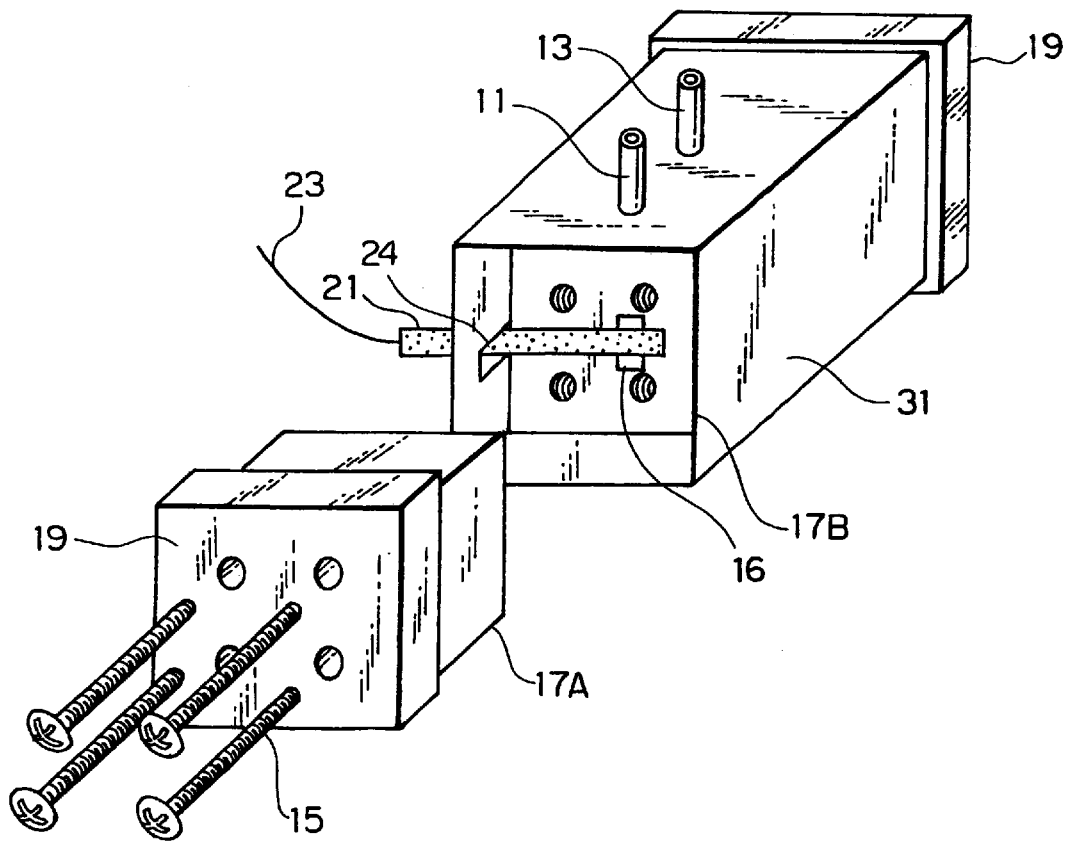
FIG. 13 is an exploded perspective view of the measurement cell shown in FIG. 9.

Referring to FIG. 13 showing an exploded view of the measurement cell 30, the solid body 17 of the sensor assembly 32 has two block pieces 17A and 17B coupled together by screws 15 together with the stopper 19. The sensor support 21 extends from outside through the opening 24 into the solid body 17 and is supported between the two block pieces 17A and 17B of the solid body 17. The two block pieces 17A and 17B are coupled, with a gasket (not shown) and sensor 16 being sandwiched therebetween. The liquid passages 20a and 20b are formed in the block piece 17B, with an opening for the first passage 20a being exposed from the surface of the blockpiece 17B.

Figure 14A:
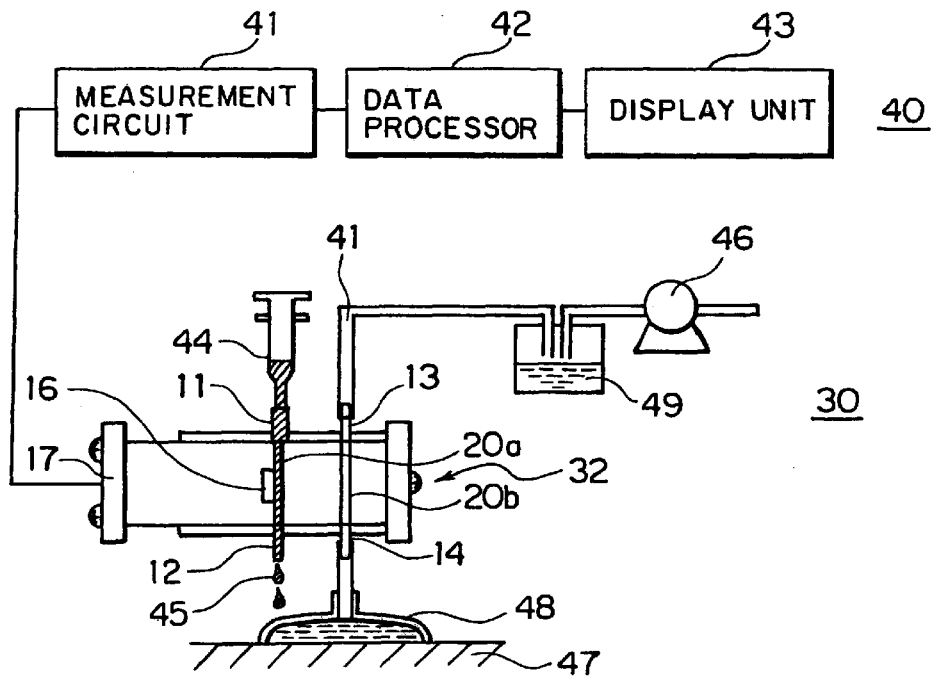
FIGS. 14A and 14B are other schematic sectional views of the measurement instrument of FIG. 9 during calibration and sampling, respectively.
Figure 14B:
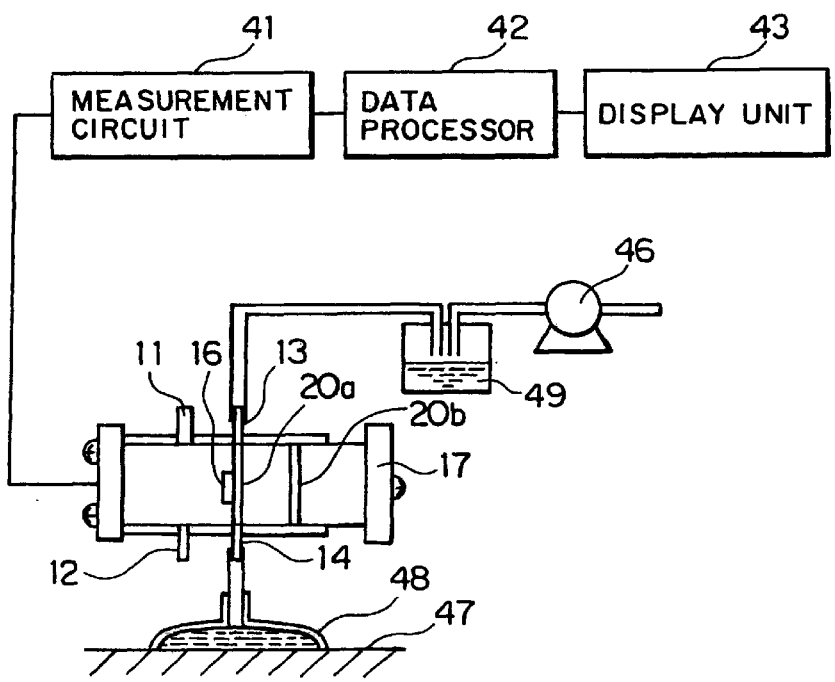

Referring to FIGS. 14A and 14B, operation of the measurement instrument according to the present embodiment will be described. FIG. 14A shows an calibration operation, wherein the sensor assembly 32 is located at the first position to align the first passage 20a having the sensor 16 with the reference liquid inlet 11 and the reference liquid outlet 12, and align the second passage 20b with the sample liquid inlet 14 and the sample liquid outlet 13. The tip of a syringe 44 is inserted in the reference liquid inlet 11 for supplying a reference liquid 45. A pipette or any other instrument can be used instead of the syringe 44. Any amount of the reference liquid can be discharged smoothly from the reference liquid outlet 12 by gravity. The reference liquid outlet 12 can be directly connected to a waste tank with a tube for discharging the reference liquid. While sensor calibration is being conducted, a pump 46 may be started by using the second passage 20b for preparation of the sampling.

FIG. 14B shows a sampling and measurement operation, wherein the sensor assembly 32 is at the second position to align the first passage 20a with the sample liquid inlet 14 and the sample liquid outlet 13. A body fluid is sampled by the pump 46 from a human skin 47 through a body fluid sampling cell 48 and the sample liquid inlet 14 to the first passage 20a, wherein the sensor 16 detects a specific ingredient in the sample liquid. The sample liquid is drained from the first passage 20a after the measurement by the sensor 16 trough the sample liquid outlet 13 and a tube to the reservoir 49. The reservoir 49 functions for reducing load of the pump 46.

Cleaning of the surface of the sensor 16 and inside the passage 20a is not generally required in the present embodiment because the sampling and measurement can be performed continuously by passing the sample liquid through the liquid passage 20a. The liquid passage 20a is of a simple structure having a small void volume which passes the body fluid quickly for effecting self cleaning and rinsing functions. Measuremrent can be recorded simply after the indicator reading is stabilized.

The body fluid sampling cell 48 has a wide opening to be attached onto the human skin 47 and a space for temporarily storing extracted body fluid for supplying the same to the liquid passage 20a.

In the above embodiment, the measurement of a specific ingredient in a body fluid can be performed continuously, whereas the sensor calibration may be performed at any time for assuring the accuracy of the sensor 16.

Sensor of any type may be selected and installed in the sensor assembly 32 in the present embodiment depending on a target ingredient in the body fluid to be measure such as sweat, blood, suction effusion fluid, interstitial fluid, extracted fluid from skin or a mucous membrane.

Figure 15:
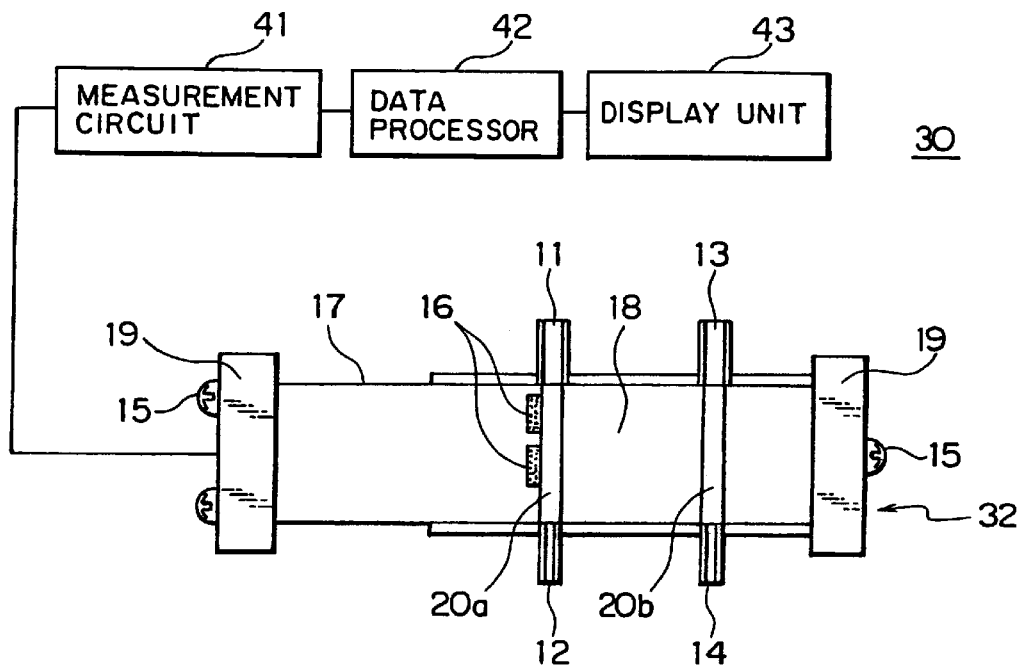
FIG. 15 is schematic sectional view of a measurement instrument according to a second embodiment of the present invention.

Referring to FIG. 15, a measurement instrument according to a second embodiment of the present invention is similar to the first embodiment except that a plurality of sensors 16 are disposed along the first passage 20a in the direction of the liquid flow. The number of sensors 16 and their locations can be selected depending on the number of target ingredients and dimensions of the sensors 16 and the liquid passage 20a.

The plurality of sensors 16 can measure a plurality of ingredients simultaneously and continuously. A reference liquid can be supplied from a syringe 44 corresponding to one of the sensors 16 to be calibrated.

According to the first and the second embodiments of the present invention, target ingredients in a liquid can be continuously measured with accuracy. The measurement instrument has a sole structure which enables easy replacement of the sensor.

EXAMPLES

Several sample liquids are measured by using the measurement instruments of the present invention as follows:

Example 1

Liquid measurement instruments fabricated based on the structure of FIG. 9 had a glucose sensor, a lactic acid sensor, a pH sensor and an uric acid sensor, respectively. The body fluid sampling cell of the liquid measurement instrument was attached to an upper arm of an adult (male, 31 years old, weight 67 kg) for measuring glucose, lactic acid, pH or uric acid in the body fluid extracted at every 10 minutes in two hours (sample number n=12). The same ingredients were also measured by using a conventional diagnostic test instrument (Hitachi automated analyzer 70050) under a similar condition. The results of each ingredient were evaluated in correlation by using a regression analysis and shown in Table 1.

TABLE 1

| Sensors used | Correlation Coefficients (n = 12) |
| --- | --- |
| Glucose sensor | 0.961 |
| Lactic acid sensor | 0.945 |
| pH sensor | 0.918 |
| Uric acid sensor | 0.933 |

Example 2

Liquid measurement instruments fabricated based on the structure of FIG. 15 included following combinations of sensors:

(1) glucose and lactic acid sensors;

(2) glucose, lactic acid and pH sensors; and (3) glucose, lactic acid, pH and uric acid sensors.

The body fluid sampling cell of the liquid measurement instrument was attached to an upper arm of an adult (male, 31 years old, weight 67 kg) for measuring glucose, lactic acid, pH or uric acid in suction effusion fluid at every 10 minutes in two hours. The same ingredients were also measured by using a conventional diagnostic test instrument under a similar condition. The results of each ingredient were evaluated in correlation by using a regression analysis and shown in Table 2, wherein data obtained by a single glucose sensor in the measurement instrument of FIG. 9 is shown by reference.

TABLE 2

| Sensors used | | Correlation Coefficients (n = 12) |
| --- | --- | --- |
| Glucose sensor | | 0.961 |
| Combination (1) | Glucose | 0.943 |
| | Lactic acid | 0.921 |
| Combination (2) | Glucose | 0.922 |
| | Lactic acid | 0.925 |
| | pH | 0.917 |
| Combination (3) | Glucose | 0.913 |
| | Lactic acid | 0.924 |
| | pH | 0.949 |
| | Uric acid | 0.935 |

Example 3

The solid body of the sensor assembly was fabricated from ABS plastic material, and the passages in the solid body were treated with respective hydrophobic materials which included paraffin, silicone and perfluorocarbon. The paraffin was heated up to 50° C. for coating the passages, silicone was diluted to 50% with pure water for coating the passages, and perfluorocarbon (Fluorad FC-722 of Sumitomo 3M) was used intact for coating the passages.

The measurement instrument based on the structure shown in FIG. 9 had the central solid bodies of the sensor assembly as mentioned above and a lactic acid sensor for evaluating the effectiveness of hydrophobic coatings in the passages. The results are shown in Table 3, wherein time length for obtaining readings of the measurements are listed in connection with the treatments.

TABLE 3

| Hydrophobic Coating | Time (sec.) |
| --- | --- |
| No treatment | 192 |
| Paraffin | 144 |
| Silicone | 77 |
| Perfluorocarbon | 74 |

Example 4

Figures 16A, 16B, 16C:
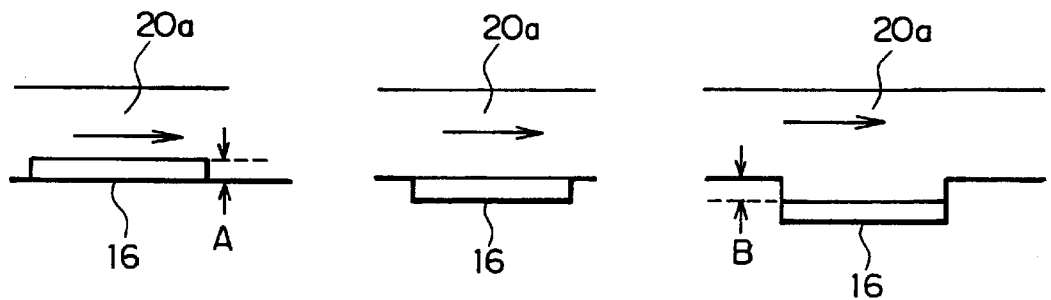
FIGS. 16A, 16B and 16C are schematic sectional views for showing the positional relationship between the inner surface of the liquid passage and the sensor shown in FIG. 15.

The measurement instruments each having a lactic acid sensor were fabricated based on the common structure of FIG. 9. The instruments had different positions of the lactic acid sensors, as shown in FIGS. 16A, 16B and 16C for evaluating the effectiveness of the positions of the sensors with respect to the inner surface of the liquid passage 20a. A sample liquid having a known lactic acid concentration was supplied at a flow rate of 0.1 milliliter/minute (ml/min.) in the passage. Each passage had a round section of 2.0 mm diameter and 30 mm length. The dimensions of the sensor were 1.2×10×0.05 mm, whereas the step "A" in FIG. 16A and the step "B" in FIG. 16C were 0.05 mm. Table 4 shows the results of correlations which are listed in connection with the configurations of the passages.

TABLE 4

| Sensor Configurations | Correlation Coefficients (n = 12) |
| --- | --- |
| FIG. 16A | 0.923 |
| FIG. 16B | 0.898 |
| FIG. 16C | 0.651 |

Example 5

Time length required for replacing sample liquid was evaluated in the structure shown in FIGS. 16A, 16B and 16C by introducing a sample liquid having known lactic acid concentrations in the passages with flow rate of 0.1 ml/min. Time lengths were measured until a stabilized readings were observed after the sample liquid was changed. Table 5 shows an average time length and the standard deviation thereof listed in connection with the configurations of the passages.

TABLE 5

| Sensor Configurations | Time length |
| --- | --- |
| FIG. 16A | 8 ± 1 sec. |
| FIG. 16B | 11 ± 1.5 sec. |
| FIG. 16C | 36 ± 4 sec. |

Example 6

Liquid measurement instruments similar to Example 4 were fabricated each having a glucose sensor, for evaluating air bubbles or impurities (such as protein) on the passage wall. The body fluid sampling cell of the measurement instrument was attached to an upper arm of an adult (male, 31 years old, weight 67 kg) for measuring glucose in suction effusion fluid every 10 minutes in two hours. Number of air bubbles and number of impurities attached to the passage wall were counted, the results of which are shown in Table 6.

TABLE 6

| Sensor Configurations | Impurities | Air bubbles |
| --- | --- | --- |
| FIG. 16A | 1 | 0 |
| FIG. 16B | 11 | 20 |
| FIG. 16C | 100 or more | 36 |

The measurement instruments of the embodiments as described above achieve an advantage in that a real time measurement can be obtained due to the simple operation of switching between calibration and measurement of the instrument, which can be obtained by simply shifting the sensor assembly with respect to the casing.

The measurement instruments further achieve advantages of continuous measurement substantially without cleaning the liquid passage because of the simple structure of the liquid passage, accurate measurement which can be obtained by the facts that the sample liquid is not diluted and that the liquid passage has a simple structure, easy replacement of the sensor, minute amount of sample liquid required for measurement, a low cost of the instrument due to less number of constituent elements, and easy calibration which can be conducted at any time simply by shifting the sensor assembly.

Since the above embodiments are described only for examples, the present invention is not limited to the above embodiments and various modifications or alterations can be easily made therefrom by those skilled in the art without departing from the scope of the present invention.

What is claimed is:

1. A measurement instrument comprising a casing having a first liquid inlet and a first liquid outlet opposed to each other and a second liquid inlet and a second liquid outlet opposed to each other, a sensor assembly having a telescope member slidably telescoped in said casing between a first position and a second position, a liquid passage formed in said telescope member, said liquid passage being aligned with said first liquid inlet and said first liquid outlet at said first position of said telescope member and aligned with said second liquid inlet and said second liquid outlet at said second position of said telescope member, at least one sensor supported by said telescope member and exposed in said liquid passage.

2. A measurement instrument as defined in claim 1, wherein said liquid inlets, said liquid outlets and said liquid passage have substantially the same cross-section.

3. A measurement instrument as defined in claim 1, wherein said telescope member has a first stopper against said casing corresponding to said first position and a second stopper corresponding to said second position.

4. A measurement instrument as defined in claim 1, wherein said liquid passage extends substantially perpendicular to a sliding direction of said telescope member with respect to said housing.

5. A measurement instrument as defined in claim 1, further comprising a dummy passage aligned with said second liquid inlet and said second liquid outlet at said first position of said telescope member.

6. A measurement instrument as defined in claim 1, said sensor has a surface substantially flush with an inner surface of said liquid passage.

7. A measurement instrument as defined in claim 1, wherein said at least one sensor include a plurality of sensors arranged along said liquid passage.

8. A measurement instrument as defined in claim 1, wherein said telescope member comprises a plurality of pieces coupled together by a fastener.

9. A measurement instrument as defined in claim 1, wherein sensor is detachably mounted by said telescope member.

10. A measurement instrument as defined in claim 1, wherein said liquid passage has a hydrophobic property.

11. A measurement instrument as defined in claim 1, wherein said sensor detects a specific ingredient in a liquid passing said liquid passage.

12. A measurement instrument as defined in claim 11, wherein said liquid is a body fluid sampled from a living body.

13. A measurement instrument as defined in claim 11, wherein said liquid is extracted through a skin of the living body.

* * * * *